(12) United States Patent
Zhao et al.

(10) Patent No.: US 12,265,658 B2
(45) Date of Patent: Apr. 1, 2025

(54) METHOD, DEVICE AND STORAGE MEDIUM FOR EVALUATING INTELLIGENT HUMAN-MACHINE COOPERATION SYSTEM

(71) Applicant: KINGFAR INTERNATIONAL INC., Beijing (CN)

(72) Inventors: Qichao Zhao, Beijing (CN); Ran Yang, Beijing (CN)

(73) Assignee: KINGFAR INTERNATIONAL INC., Beijing (CN)

( * ) Notice: Subject to any disclaimer, the term of this patent is extended or adjusted under 35 U.S.C. 154(b) by 0 days.

(21) Appl. No.: 18/378,930

(22) Filed: Oct. 11, 2023

(65) Prior Publication Data

US 2024/0053826 A1     Feb. 15, 2024

Related U.S. Application Data

(63) Continuation of application No. PCT/CN2023/112288, filed on Aug. 10, 2023.

(30) Foreign Application Priority Data

Aug. 12, 2022    (CN) ......................... 202210967645.7

(51) Int. Cl.
    *G06F 3/01*        (2006.01)
(52) U.S. Cl.
    CPC ................... *G06F 3/015* (2013.01)
(58) Field of Classification Search
    CPC ...................................................... G06F 3/015
    See application file for complete search history.

(56) References Cited

U.S. PATENT DOCUMENTS

| | | |
|---|---|---|
| 2011/0270123 A1 | 11/2011 | Reiner |
| 2019/0227626 A1 | 7/2019 | Mohammadrezazadeh et al. |

(Continued)

FOREIGN PATENT DOCUMENTS

| | | |
|---|---|---|
| CN | 103971311 A | 8/2014 |
| CN | 113435116 A | 9/2021 |

(Continued)

OTHER PUBLICATIONS

International Search Report of Corresponding PCT Application No. PCT/CN2023/112288; Oct. 24, 2023; 4 Pgs.

(Continued)

*Primary Examiner* — Kwang-Su Yang
(74) *Attorney, Agent, or Firm* — Cooper Legal Group, LLC (57) ABSTRACT

The present disclosure provides an evaluation method, device, and storage medium for intelligent human-machine cooperation system, the method comprises the following steps: recording a real-time objective data of subject during an execution of the intelligent human-machine cooperation system test; inputting the objective data into a pre-trained fitting model to predict and obtain a subjective evaluation of a prediction, the pre-trained fitting model is based on a recorded objective data and subjective evaluation fitting, and the subjective evaluation is obtained based on a first subjective evaluation result of the subject after executing the intelligent human-machine cooperation system test for pre-training; obtaining a real-time human-machine cooperation score based on a predicted subjective evaluation.

10 Claims, 3 Drawing Sheets

--- recording objective data of a subject during executing, by the subject, an intelligent human-machine cooperation system test    / S110

↓ inputting the objective data into a pre-trained fitting model for prediction to obtain a predicted subjective evaluation, wherein the pre-trained fitting model is obtained by fitting the recorded objective data and the subjective evaluation, and the subjective evaluation is obtained based on a first subjective evaluation result of the subject after executing the intelligent human-machine cooperation system test for a pre-training    / S120

↓ obtaining a real-time human-machine cooperation score based on the predicted subjective evaluation test    / S130

(56) References Cited

U.S. PATENT DOCUMENTS

| | | | |
|---|---|---|---|
| 2019/0313959 A1 | 10/2019 | Durkee et al. | |
| 2020/0204862 A1 | 6/2020 | Miller | |
| 2020/0243102 A1* | 7/2020 | Schmidt | G10L 19/005 |
| 2020/0250511 A1 | 8/2020 | Hu | |
| 2022/0233244 A1 | 7/2022 | Shelton, IV et al. | |
| 2023/0070665 A1* | 3/2023 | Day | A61B 5/7264 |
| 2024/0161645 A1* | 5/2024 | Yu | G06F 9/453 |

FOREIGN PATENT DOCUMENTS

| | | |
|---|---|---|
| CN | 114356095 A | 4/2022 |
| CN | 115407872 A | 11/2022 |

OTHER PUBLICATIONS

Supplementary European Search Report received in corresponding European Patent Application No. 23782723.3, dated Sep. 17, 2024, 4 pages.

* cited by examiner

METHOD, DEVICE AND STORAGE MEDIUM FOR EVALUATING INTELLIGENT HUMAN-MACHINE COOPERATION SYSTEM

CROSS-REFERENCE TO RELATED APPLICATION

The present application claims a continuation of PCT application No. PCT/CN2023/112288, filed on Aug. 10, 2023, which claims the priority and benefit of Chinese patent application No. 202210967645.7, filed on Aug. 12, 2022. The entirety of PCT application No. PCT/CN2023/112288 and Chinese patent application No. 202210967645.7 are hereby incorporated by reference herein and made a part of this specification.

TECHNICAL FIELD

The present disclosure generally relates to the technical field of intelligent human-machine cooperation, and in particular, to a method, device, and storage medium for evaluating intelligent human-machine cooperation system.

BACKGROUND ART

With rapid development of artificial intelligence technology, an intelligent human-machine cooperation system will generally exist in many aspects such as intelligent manufacturing, smart transportation, and intelligent life, the intelligent human-machine cooperation system takes human and machine as a team, integrating human intelligence and artificial intelligence, and achieving autonomous human-machine interaction and win-win cooperation, based on the Brain Computer Interface (BCI), an information exchange between a brain or nervous system of organic life forms and computers is achieved, the intelligent human-machine cooperation based on BCI paradigm is executed, however, how to evaluate an effect of the interaction and collaboration relationship formed between the human and the intelligent human-machine cooperation system will affect an user experience and an ability of the intelligent human-machine cooperation system.

An existing method for evaluating the human-machine cooperation system only evaluate the intelligent human-machine cooperation system based on the BCI by selecting an information transmission rate and accuracy of the system, which is insufficient to sufficiently, comprehensively, and rigorously evaluate the intelligent human-machine cooperation system.

Therefore, how to provide a comprehensive, sufficient, and rigorous method for evaluating the intelligent human-machine cooperation system is an urgent problem to be solved.

SUMMARY

In order to overcome the problem in the related art, the present disclosure provides an evaluation method, device, and storage medium for intelligent human-machine cooperation system to eliminate or improve one or more defects existing in the prior art.

According to a first aspect of embodiments of the present disclosure, there is provided a method for evaluating an intelligent human-machine cooperation system, comprising:

recording, in real-time, objective data of a subject during executing, by the subject, an intelligent human-machine cooperation system test;

inputting the objective data into a pre-trained fitting model for prediction to obtain a predicted subjective evaluation, wherein, the pre-trained fitting model is obtained by fitting the recorded objective data and the subjective evaluation, and the subjective evaluation is obtained based on a first subjective evaluation result of the subject after executing the intelligent human-machine cooperation system test for a pre-training; and obtaining a real-time human-machine cooperation score based on the predicted subjective evaluation.

In some embodiments of the present disclosure, the method further includes: generating a real-time objective evaluation based on the objective data of the subject recorded in real-time, and obtaining the real-time human-machine cooperation score by combining the real-time objective evaluation with the predicted subjective evaluation;

the obtaining the real-time human-machine cooperation score by combining the real-time objective evaluation with the predicted subjective evaluation comprises standardizing and summing, according to preset weight values, the real-time objective evaluation and the predicted subjective evaluation.

In some embodiments of the present disclosure, the objective data comprises one or more of behavior data, eye movement data, and physiological data of the subject; the behavior data comprises one or more of: a reaction time, an accuracy rate, a false alert rate, and a behavioral performance indicator customized according to scenarios; the eye movement data comprises one or more of: the reaction time, a fixation point, and a fixation time; the physiological data comprises one or more of: an electrodermal data, an electroencephalogram data, and a heart rate data.

In some embodiments of the present disclosure, the subjective evaluation is further obtained based on a second subjective evaluation result of the subject before executing the intelligent human-machine cooperation system test for pre-training, forms of the first and second subjective evaluation results is in a form of a questionnaire, a scale, and/or a paradigm.

In some embodiments of the present disclosure, the standardizing the real-time objective evaluation and the predicted subjective evaluation comprises: eliminating dimensional differences by converting the real-time objective evaluation and the predicted subjective evaluation into dimensionless pure numerical values; standardizing data by scaling the real-time objective evaluation and the predicted subjective evaluation in a form of the dimensionless pure numerical values according to a preset proportion.

In some embodiments of the present disclosure, obtaining the pre-trained fitting model by fitting the recorded objective data and the subjective evaluation comprises: generating, with a modeling analysis method, the fitting model for predicting a relationship between an independent variable and a dependent variable, wherein, the independent variable is the objective data of the subject recorded in real-time, and the dependent variable is the predicted subjective evaluation.

In some embodiments of the present disclosure, the method further comprises adjusting a relationship between signal instructions and an external hardware device control during the intelligent human-machine cooperation system test based on the real-time human-machine cooperation score; the relationship between the signal instructions and the external hardware device control comprises a signal recognition threshold and a signal output gain.

In some embodiments of the present disclosure, the intelligent human-machine cooperation system test is a human-machine interaction between the subject and the intelligent human-machine cooperation system, the intelligent human-machine cooperation system is built based on a task framework in a prototype library, a standard library, and a paradigm library, the task framework comprises a processor and a controller; the processor is configured to acquire preset types of brain signals of the subject, and extract evoked signals based on the brain signals and a BCI (Brain-Computer Interface) paradigm library and generate a control instruction based on the evoked signals; the controller is configured to control the external hardware device to execute the control instruction.

According to the second aspect of embodiments of the present disclosure, there is provided a device for evaluating an intelligent human-machine cooperation system, comprising a processor and a storage with computer instructions stored therein, wherein the processor is configured to execute the computer instructions stored in the storage to implement the methods described in the above embodiments.

In an aspect, the present disclosure provides non-transitory computer-readable storage medium with a computer program stored thereon, wherein the computer program is configured to be executed by a processor to implement the methods described in the above embodiments.

The evaluation method, device, and storage medium for the intelligent human-machine cooperation system of the present disclosure can overcome an one-sidedness of existing evaluation methods, and comprehensively, rigorously, and objectively evaluate the intelligent human-machine cooperation system, the intelligent human-machine cooperation system evaluation is executed based on the real-time objective data through the fitting models.

The method for evaluating the intelligent human-machine cooperation system of the present disclosure can integrate the one-sidedness of the existing evaluation methods, fully, comprehensively, and rigorously evaluate the intelligent human-machine cooperation system.

Additional advantages, purposes, and features of the present disclosure will be partially explained in the following description, and will partly become apparent to those skilled in the art after studying the following, or can be learned from a practice of the present disclosure. The purpose and other advantages of the present disclosure can be achieved and obtained through specific structures indicated in a description and accompanying drawings.

BRIEF DESCRIPTION OF THE DRAWINGS

The accompanying drawings described herein are intended to provide a further understanding of the present disclosure and form a part of the present disclosure, and do not form a limitation of the present disclosure. In the accompanying drawings.

DETAILED DESCRIPTION

In order to make a purpose, a technical solution, and an advantage of the present disclosure more clearly, the following will be further described in detail below with reference to accompanying drawings and embodiments. Herein, schematic embodiments and explanations of the present disclosure are only used to explain the present disclosure and are not intended to limit it.

Herein, it should also be noted that in order to avoid blurring the present disclosure due to unnecessary details, only structures and/or processing steps closely related to a scheme according to the present disclosure are shown in the accompanying drawings, while other details that are not closely related to the present disclosure are omitted.

It should be emphasized that the term "including/containing" when used in the article refers to an existence of features, elements, steps, or components, but does not exclude the existence or attachment of one or more other features, elements, steps, or components.

Herein, it should also be noted that, if there are no special instructions, the term "connection" in the article can not only refer to a direct connection, but also to an indirect connection with an intermediate object.

In the following text, the embodiments of the present disclosure will be described with reference to the accompanying drawings. In the accompanying drawings, the same reference signs represent the same or similar components, or the same or similar steps.

In order to overcome a problem of insufficient comprehensive evaluation methods for existing intelligent human-machine cooperation system, the present disclosure provides a method for evaluating an intelligent human-machine cooperation system, which is based on an objective data recorded by subject during a process of executing the intelligent human-machine cooperation system test, and a subjective evaluation result of the subject after executing the intelligent human-machine cooperation system test for pre-training, and trains to obtain a fitting model, which inputs a real-time objective data to obtain a predicted subjective evaluation, and then obtain a real-time human-machine cooperation score.

Figure 1:
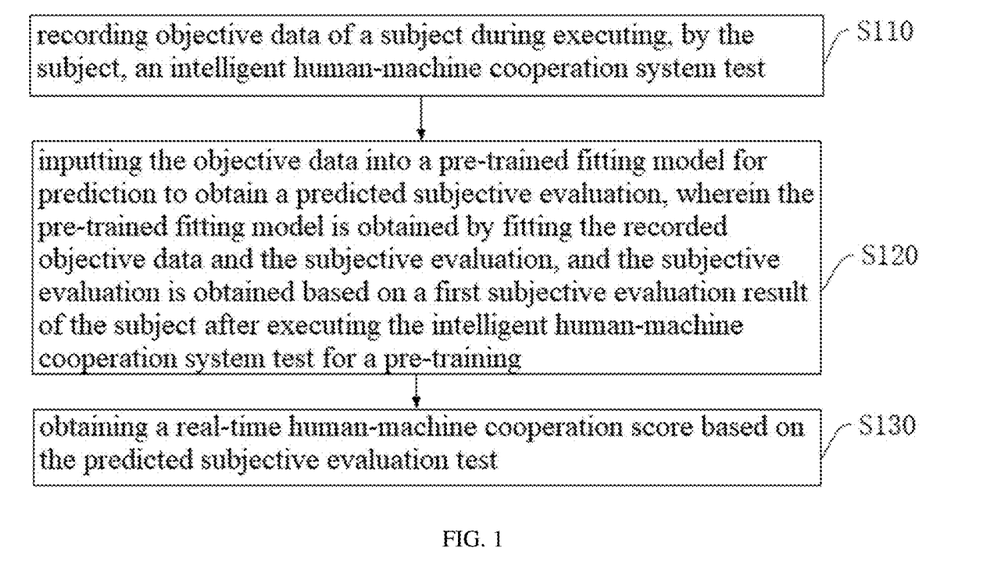
FIG. 1 is a flowchart of a method for evaluating an intelligent human-machine cooperation system according to an embodiment of the present disclosure.

FIG. 1 is a flowchart of the method for evaluating intelligent human-machine cooperation system in the embodiment according to the present disclosure, which includes the following steps:

step S110: recording objective data of a subject during executing, by the subject, an intelligent human-machine cooperation system test.

The above objective data includes one or more of a behavior data, an eye movement data, and a physiological data of the subject, and the behavior data includes one or more of: a reaction time, an accuracy rate, a false alert rate, and a behavioral performance indicator customized according to scenarios. The eye movement data includes one or more of the following: the reaction time, a fixation point, and a fixation time. The physiological data includes one or more of: electrodermal data, electroencephalogram data, and heart rate data. Integrating objective information from multiple dimensions, states of the subject and results of the intelligent human-machine cooperation system test can be showed in a very objective and comprehensive manner.

Taking the scenario of a robotic arm designed for people with disabilities as an example, the intelligent human-machine cooperation system is configured to explain the above terms, the reaction time is a time from a command given by the subject to a reaction of a mechanical arm, the accuracy rate is a response accuracy rate of the mechanical arm to the command given by the subject, and the false alert rate is proportion of erroneous signals detected in signals greater than a threshold. In individual scenarios, certain data may not be used, such as the fixation point and the fixation time, the physiological data is configured to determine whether to collect based on demand, such as in auxiliary intelligent devices for combat scenarios, where the physiological data of the subject needs to be collected.

The electrodermal data includes a skin conductivity level (SCL) and a skin conductivity response (SCR), as well as their mean, maximum, minimum, standard deviation, variance, and polar distance. The heart rate data includes a heart rate variability (HRV), an average heart rate, and a standard deviation of continuous heart beat interval. In particular, the heart rate variability HRV can be a SDNN (standard deviation of RR interval for all sinus beats), a RMSSD (root mean square of a difference between adjacent RR intervals), a VLF (extremely low frequency), a LF (low frequency), a LF (NU), a HF (high frequency), a HF (NU), and a LF/HF, etc., where the NU represents a normalized value, with LF (NU)=LF (/total power-VLF) and HF (NU)=HF (/total power-VLF). The electroencephalogram data includes electroencephalogram signals of different rhythms $\delta$、$\theta$、$\alpha$、$\beta$ wave. In particular, the frequency of the $\delta$ wave is 1-4 Hz, the frequency of the $\theta$ wave is 4-8 Hz, the frequency of the $\alpha$ wave is 8-12 Hz, the frequency of the $\beta$ wave is 13-30 Hz. It is also possible to calculate the relative power index of four different wave bands of the electroencephalogram signals, that is, the proportion of power in different wave bands to the total power value (the sum of $\delta$, $\theta$, $\alpha$ and $\beta$). In the other embodiment, the physiological data also includes an electromyographic data EMG, which can be mean value (Mean), maximum (Max), minimum (Min), standard deviation (s), variance ($s^2$), root mean square (RMS), mean absolute value (MAV), and integral electromyographic value (IEMG).

It should be noted that the present disclosure is not limited to this, and a specific information contained in the objective data is only an example, for example, the physiological data can also include a respiratory data and a skin temperature data, and the electroencephalogram data can also include a near-infrared spectroscopy and an electroencephalogram, the objective data that can be collected by those skilled in the art belongs to a scope of a protection of the present disclosure. A diversity of the objective data available for selection, combined with a specific scenario for a personalized selection, expands a scope of application of the present disclosure.

step S120: inputting the objective data into a pre-trained fitting model for prediction to obtain a predicted subjective evaluation, the pre-trained fitting model is obtained by fitting the recorded objective data and the subjective evaluation, and the subjective evaluation is obtained based on a first subjective evaluation result of the subject after executing the intelligent human-machine cooperation system test for a pre-training.

In the embodiment of the present disclosure, the method further includes obtaining the subjective evaluation result of the subject before executing the intelligent human-machine cooperation system test, generating the subjective evaluation based on the subjective evaluation result of the subject after executing the intelligent human-machine cooperation system test and the subjective evaluation result of the subject before executing the intelligent human-machine cooperation system test. The subjective evaluation result of the subject before executing the intelligent human-machine cooperation system test is configured as a baseline to increase the accuracy of the subjective evaluation.

In the embodiment of the present disclosure, the subjective evaluation is further obtained based on a second subjective evaluation result of the subject before executing the intelligent human-machine cooperation system test for pre-training. Each of the first and second subjective evaluation results is in a form of a questionnaire, a scale, and/or a paradigm. Through the subjective evaluation, the actual feelings of the subject can be learned, which takes care of the subjective feelings of the subject, in practical production design, it is very necessary to take care of the subjective feelings of the subject/users in many application scenarios (such as the mechanical arm and joint for people with a disabled).

Specifically, in the embodiment of the present disclosure, the subjective evaluation is a questionnaire, which is a NASA-TLX (Task Load Index) cognitive load measurement questionnaire. The questionnaire is only an example, and the present disclosure is not limited to this, it can also be an acceptable questionnaire in other industries.

The step of obtaining the pre-trained fitting model by fitting the recorded objective data and the subjective evaluation comprises generating, with a modeling analysis method, the fitting model for predicting a relationship between an independent variable and a dependent variable; the independent variable is the objective data of the subject recorded in real-time, and the dependent variable is the predicted subjective evaluation. Specifically, the modeling analysis method is a regression analysis method. The regression analysis method is based on a large amount of historical data, after a comprehensive analysis, the fitting model is established to make the fitting model representative and capable of accurately associating the objective data and the predictive subjective evaluation with high probability.

step S130: obtaining a real-time human-machine cooperation score based on the predicted subjective evaluation.

In the embodiment of the present disclosure, the method further includes: generating a real-time objective evaluation based on the objective data of the subject recorded in real-time, and obtaining the real-time human-machine cooperation score by combining the real-time objective evaluation with the predicted subjective evaluation; the obtaining the real-time human-machine cooperation score by combining the real-time objective evaluation with the predicted subjective evaluation comprises standardizing and summing, according to preset weight values, the real-time objective evaluation and the predicted subjective evaluation.

In the embodiment of the present disclosure, the predicted subjective evaluation is directly configured as the real-time human-machine cooperation score. In an embodiment of the present disclosure, the real-time objective evaluation is generated based on the objective data of the subject recorded in real-time, the real-time objective evaluation and the predicted subjective evaluation are standardized and summed according to preset weight values to generate the real-time human-machine cooperation score.

In the embodiment of the present disclosure, the step of standardizing the real-time objective evaluation and the predicting subjective evaluation includes eliminating dimensional differences and standardizing data. Further, eliminating dimensional differences includes converting the real-time objective evaluation and the predicted subjective evaluation into dimensionless pure numerical values; the standardizing data includes scaling the real-time objective evaluation and the predicted subjective evaluation in a form of the dimensionless pure numerical values according to a preset proportion. The method can combine the objective data with the subjective feelings of the subject, and combine the two to obtain the comprehensive evaluation result of the intelligent human-machine cooperation system. Eliminating dimensional differences and standardizing data can unify resulting values, facilitating subsequent operations.

In the embodiment of the present disclosure, the step of fitting the recorded objective data with the subjective evaluation to obtain a pre-trained fitting model includes generating, with a modeling analysis method, such as the regression analysis method, the fitting model for predicting the relationship between an independent variable and a dependent variable, in particular the independent variable is the objective data of the subject recorded in real-time, and the dependent variable is the predicted subjective evaluation. It should be noted that the fitting model is a predictive model, which fits the objective data collected offline to the subjective evaluation through the regression analysis method, thereby obtaining a correlation between the objective data and the human-machine cooperation score, executing the prediction based on the objective data of the subject recorded in real-time, and the real-time human-machine cooperation score is generated. In particular, the objective data collected offline refers to a certain amount of non-real-time objective data collected, and the correlation between the objective data and the human-machine cooperation score is obtained through the regression analysis method. Through the regression analysis method, based on a certain amount of offline data, an objective, stable, and credible fitting model is obtained, which can quickly associate the real-time objective data with the predicted subjective evaluation.

There are three methods for constructing the fitting model:
1. Threshold Method

Setting different thresholds for different objective data and meeting a certain threshold that is determines a level of the subjective evaluation. Based on known objective data and the subjective evaluation, the threshold can be calculated based on the objective data and the corresponding subjective evaluation, thereby obtaining the threshold (or a plurality thresholds) that can predict the subjective evaluation based on the objective data.

2. Modeling Method

Referring to the following formula for modeling:

$$\hat{y}(\omega,x)=\omega_0+\omega_1 x_1+ \ldots +\omega_p x_p$$

In particular y (w, x) is a subjective measurement result; the x values ($x_1, \ldots, x_p$) are physiological data vectors (EEG, HRV, EDA, EMG, etc.), and parameters $\omega_0, \omega_1 \ldots, \omega_p$ are fitted according to the above formula to obtain a model that can predict the y value.

3. Machine Learning Method

A machine learning model can include a neural network, a random forest, a k-nearest neighbor, a decision tree, a support vector machine (SVM), linear discriminant analysis (LDA), etc. The objective data can be configured as an input layer of the machine learning model, and the subjective evaluation can be configured as an output layer of the machine learning model. By training with a large amount of data, the parameters between the input layer and output layer are calculated to obtain the machine learning model that can predict the subjective evaluation.

In the embodiment of the present disclosure, the modeling analysis method is the regression analysis method, which generates the fitting model for predicting the relationship between the independent variable and the dependent variable based on a linear regression equation.

It should be noted that the present disclosure is not limited to this, and the fitting method is only an example, for example, it can also be based on a deep learning algorithm for model training, the trained model includes the relationship between the objective data of the subject and the human-machine cooperation score, based on the objective data of the tested person collected in real-time, the real-time human-machine cooperation score can be predicted.

Figure 2:
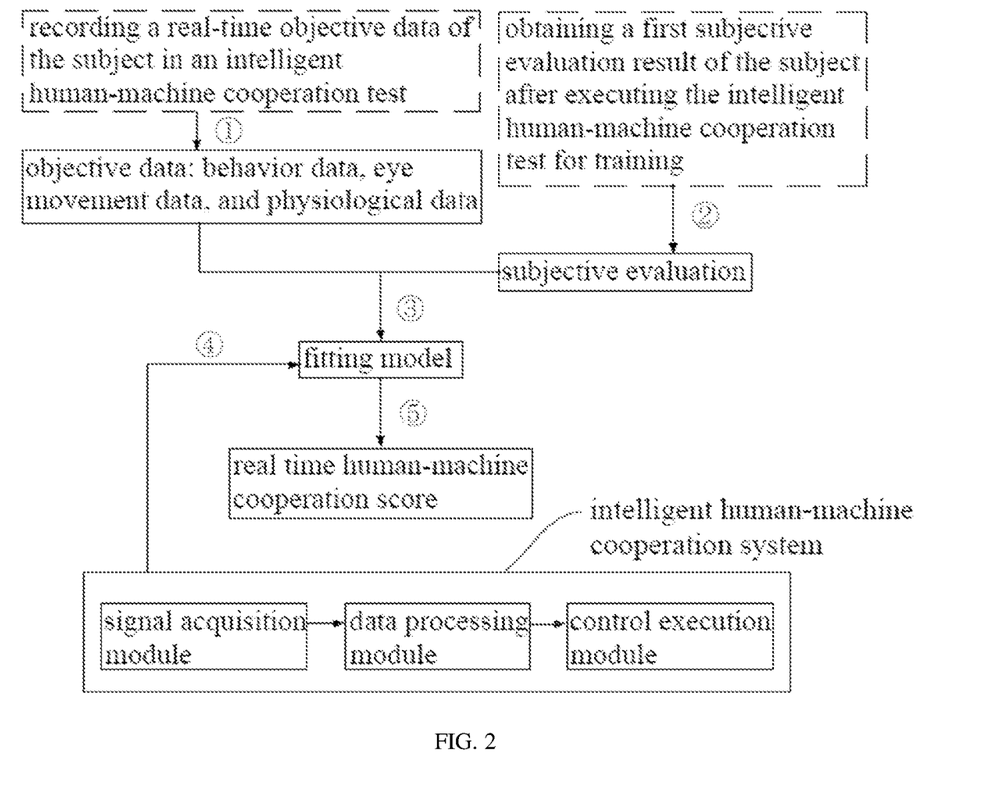
FIG. 2 is a flowchart of obtaining a real-time human-machine cooperation score according to an embodiment of the present disclosure.

FIG. 2 is a flowchart of obtaining the real-time human-machine cooperation score according to the present disclosure, which includes:
① during a testing process of the intelligent human-machine cooperation system, the objective data of the subject is recorded, including the behavior data, the eye movement data, and the physiological data;
② obtaining a subjective scale filled out by the subject after executing the intelligent human-machine cooperation system test for training, and analyzing and calculating the subjective evaluation based on the subjective scale;
③ fitting the recorded objective data with the subjective data to obtain the fitting model;
④ the intelligent human-machine cooperation system sends the real-time recorded objective data of the subject to the fitting model; in particular, the intelligent human-machine cooperation system includes a processor and a controller;
⑤ the fitting model is based on the real-time recorded objective data of the subject for prediction, and obtains the predicted subjective evaluation, the predicted subjective evaluation is directly configured as the real-time human-machine cooperation score.

In the embodiment of the present disclosure, optionally, the method further includes adjusting the relationship between signal instruction during the testing process of the intelligent human-machine cooperation system and the external hardware device control based on the real-time human-machine cooperation score.

Furthermore, in the embodiment of the present disclosure, the relationship between the signal instruction and the external hardware device control includes a signal recognition threshold and a signal output gain. For example, based on the human-machine cooperation score of a trial, which reflects the subjective feeling of the subject is fatigue, thereby reducing the signal recognition threshold and increasing the signal output gain, so that low amplitude signals can also be recognized in the fatigue state of the subject, achieving an operational control of the external hardware device.

Figure 3:
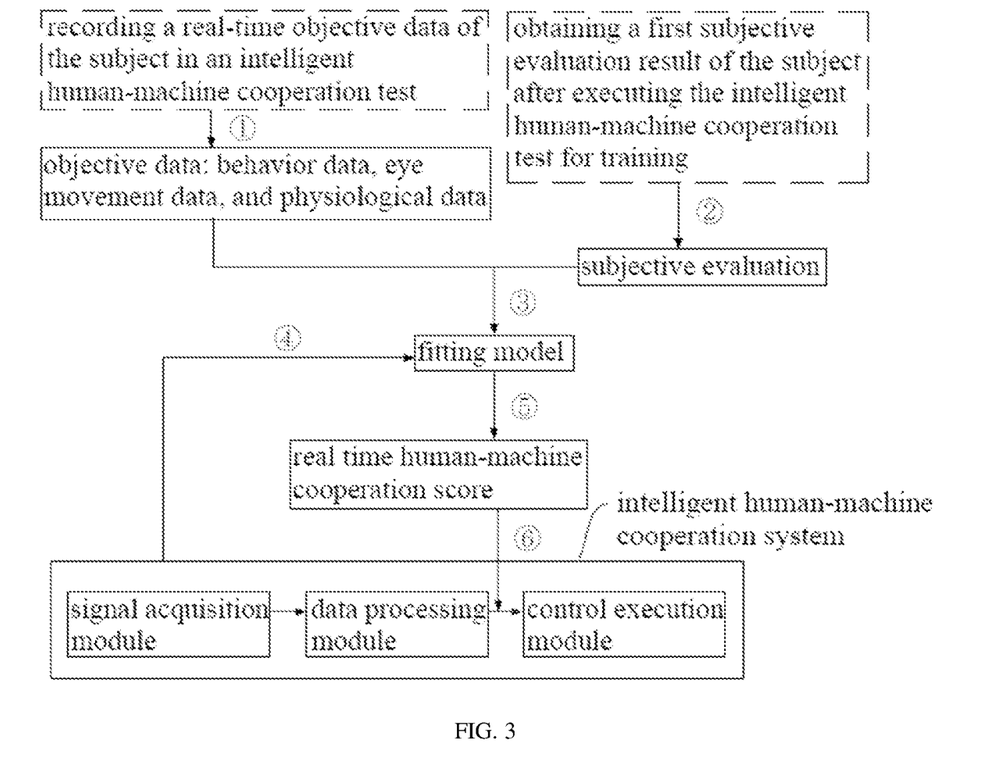
FIG. 3 is a flowchart of obtaining a real-time human-machine cooperation score according to an embodiment of the present disclosure.

FIG. 3 is a flowchart of obtaining the real-time human-machine cooperation score in an embodiment according to the present disclosure, which includes:
① during the testing process of the intelligent human-machine cooperation system, the objective data of the subject is recorded, including the behavior data, the eye movement data, and the physiological data;
② obtaining the subjective questionnaire filled out by the subject after executing the intelligent human-machine cooperation system test for training, and analyzing and calculating the subjective evaluation based on the subjective questionnaire;

③ fitting the recorded objective data with the subjective data to obtain the fitting model;

④ the intelligent human-machine cooperation system sends the real-time recorded objective data of the subject to the fitting model; in particular, the intelligent human-machine cooperation system includes the processor and the controller;

⑤ the fitting model is based on the real-time recorded objective data of the subject for prediction, and obtains the predicted subjective evaluation, the predicted subjective evaluation is directly configured as the real-time human-machine cooperation score;

⑥ the intelligent human-machine cooperation system receives the real-time human-machine cooperation score and adjusts the intelligent human-machine cooperation process based on this, that is, the relationship between the signal instruction in the human-machine cooperation testing process and the external hardware device control, the relationship between the signal instruction and the control of the external hardware device specifically includes the signal recognition threshold and the signal output gain, that is, adjusting the signal recognition threshold and the signal output gain of the signal instruction, so that the control of the external hardware device is strengthened and reduced.

In some embodiments of the present disclosure, the step ⑤ in FIG. 2 and the step ⑤ in FIG. 3 can also generate the real-time objective evaluation based on the predicted subjective evaluation and the objective data of the subject recorded in real-time, the real-time human-machine cooperation score is obtained comprehensively. By standardizing the real-time objective evaluation and the predicted subjective evaluation and adding them according to the preset weights, the real-time human-machine cooperation score is generated. Specifically, the real-time objective evaluation and the predicted subjective evaluation are added with a 1:1 weight after standardization to generate the real-time human-machine cooperation score.

In the embodiment of the present disclosure, the step of executing the human-machine cooperation testing by the subject is an interaction between the subject and the intelligent human-machine cooperation system, the intelligent human-machine cooperation system is built based on a task framework in a prototype library, a standard library, and a paradigm library, which includes the processor and the controller. In particular, the processor is configured to collect preset types of brain signals of the subject, and extract evoked signals based on the brain signals and a BCI paradigm library and generate control instructions based on the evoked signals; the controller is configured to control the external hardware devices to execute the control instructions.

Figure 4:
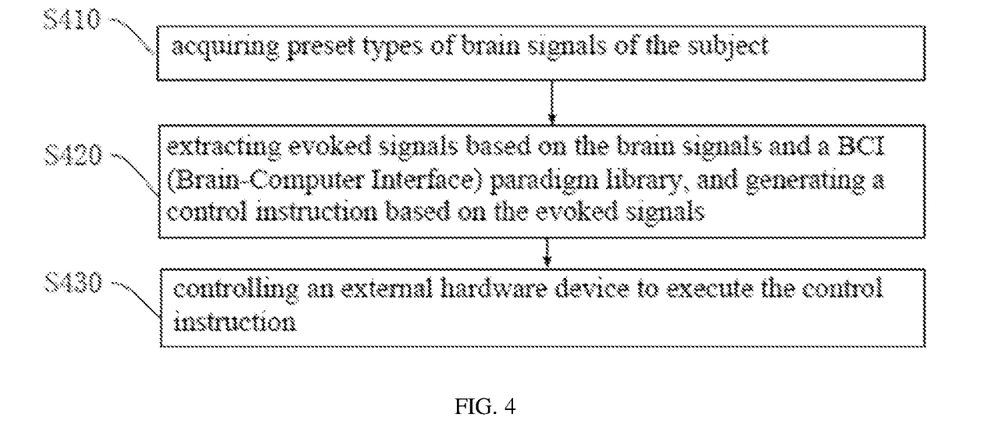
FIG. 4 is a working flowchart of the intelligent human-machine cooperation system based on BCI paradigm according to an embodiment of the present disclosure.

FIG. 4 is a working flowchart of the intelligent human-machine cooperation system based on the BCI paradigm in an embodiment according to the present disclosure, with the following steps:

step S410: acquiring, by the processor, preset types of brain signals of the subject. The types of the brain signals include one or more of the following: electroencephalography (EEG), functional magnetic resonance imaging (fMRI), near infrared spectroscopy (NIRS), MEG (Magnetoencephalogram), ECOG (Electrocardiogramd LFP (Lithium Iron phosphate).

step S420: extracting, by the processor, the evoked signals based on the brain signals and the BCI paradigm library, and generates the control instructions based on the evoked signals. The BCI paradigm library includes but is not limited to the following BCI stimulus paradigms: SCPs-BCI (Slow Cortical Potential based BCI), SMRs-BCI (Sensorimotor Rhythm based BCI), SSVEPs-BCI (Steady State Visual Evoked Potential based BCI). The types of the evoked signals include but are not limited to one or more of the following: sensory motor rhythm (SMR), event related potential, steady-state visual evoked potential (SSVEP), slow cortical potential (SCP), and error related potential.

Step S430: controlling, by the controller, the external hardware devices to execute the control instructions. In particular, the external hardware device includes but is not limited to one or more of the following: a robot, an artificial bone, a mechanical hand/arm, a brain controlled wheelchair, and a virtual reality or augmented reality.

In particular, the type of the collected brain signals, the processing of the brain signals by a BCI interface, and the subsequent operation of the processor and the controller, can be customized and set by the user, that is, according to the needs of the real scenarios, the user can independently select the type of the collected brain signals and the evoked signals to be extracted, and define the specific control instructions based on the evoked signals, sending the control instructions to the external hardware devices, controlling an execution of the external hardware devices to achieve corresponding functions.

The evaluation method, device, and storage medium for the intelligent human-machine cooperation system of the present disclosure can overcome an one-sidedness of the existing evaluation methods, and comprehensively, rigorously, and objectively evaluate the intelligent human-machine cooperation system, the intelligent human-machine cooperation system evaluation is executed based on the real-time objective data through the fitting model. The method provided by the present disclosure can achieve standardized, unified, and scientifically rigorous evaluation of the intelligent human-machine cooperation system, the method can be widely used as a standard process, and the method has a sufficient data support and combines the subjective feelings of the subject, covering comprehensively.

Correspondingly to the above method, the present disclosure also provides the device for evaluating the intelligent human-machine cooperation system, the evaluation device includes a computer device, which includes a processor and a storage; in particular the computer instructions are stored in the storage, and the processor is configured to execute the computer instructions stored in the storage, when the computer instructions are executed by the processor, the device executes the steps of the method mentioned above.

The embodiment of the present disclosure further provides a computer-readable storage medium, on which a computer program is stored, when the computer program is executed by the processor, the steps of an edge computing server deployment method mentioned above are executed. The computer-readable storage medium can be a tangible storage medium, such as a random access memory (RAM), a memory, a read-only memory (ROM), an electrically programmable ROM, an electrically erasable and programmable ROM, a register, a floppy disk, a hard disk, a removable storage disk, a CD-ROM, or any other forms of the storage medium well-known in the technical field.

Those skilled in the art should understand that the exemplary components, systems, and methods described in conjunction with the disclosed embodiments can be executed in the hardware, software, or a combination of the two. Whether to execute it in the hardware or software depends on a specific application and design constraints of the technical solution. Professional and technical personnel can use different methods to achieve the described functions for each specific application, but such implementation should not be considered beyond the scope of the present disclosure. When executed in the hardware, it can be, for example, electronic circuits, application specific integrated circuits (ASICs), appropriate firmware, plugins, function cards, etc. When executed in software, the elements of the present disclosure are programs or code segments configured to execute the required tasks. The programs or the code segments can be stored in the machine readable media, or transmitted on transmission medium or communication links through the data signals carried by carriers.

It should be clarified that the present disclosure is not limited to the specific configurations and processes described above and shown in the figures. For simplicity, detailed descriptions of known methods have been omitted herein. In the above embodiments, several specific steps are described and shown as examples. However, the method process of the present disclosure is not limited to the specific steps described and shown. Those skilled in the art can make various changes, modifications, additions, or change an order between the steps after understanding a spirit of the present disclosure.

In the present disclosure, the features described and/or exemplified for the embodiment can be used in the same or similar manner in one or more other embodiments, and/or combined or replaced with the features of other embodiments.

What is claimed is:

1. A method for evaluating an intelligent human-machine cooperation system, comprising:
    recording objective data of a subject during executing, by the subject, an intelligent human-machine cooperation system test;
    inputting the objective data into a pre-trained fitting model for prediction to obtain a predicted subjective evaluation, wherein the pre-trained fitting model is obtained by fitting the objective data and a subjective evaluation, and the subjective evaluation is obtained based on a first subjective evaluation result of the subject after executing the intelligent human-machine cooperation system test for a pre-training; and
    generating a real-time objective evaluation based on the objective data of the subject recorded in real-time, and obtaining a real-time human-machine cooperation score by combining the real-time objective evaluation with the predicted subjective evaluation,
    wherein the obtaining the real-time human-machine cooperation score by combining the real-time objective evaluation with the predicted subjective evaluation comprises standardizing and summing, according to preset weight values, the real-time objective evaluation and the predicted subjective evaluation.

2. The method according to claim 1, wherein the objective data comprises one or more of behavior data, eye movement data, or physiological data of the subject:
    the behavior data comprises one or more of a reaction time, an accuracy rate, a false alert rate, or a behavioral performance indicator customized according to scenarios;
    the eye movement data comprises one or more of a second reaction time, a fixation point, or a fixation time; or
    the physiological data comprises one or more of electrodermal data, electroencephalogram data, or heart rate data.

3. The method according to claim 1, wherein:
    the subjective evaluation is further obtained based on a second subjective evaluation result of the subject before executing the intelligent human-machine cooperation system test for the pre-training; and
    each of the first subjective evaluation result and the second subjective evaluation result is in a form of at least one of a questionnaire, a scale, or a paradigm.

4. The method according to claim 1, wherein the standardizing the real-time objective evaluation and the predicted subjective evaluation comprises:
    eliminating dimensional differences by converting the real-time objective evaluation and the predicted subjective evaluation into dimensionless pure numerical values; and
    standardizing data by scaling the real-time objective evaluation and the predicted subjective evaluation in a form of the dimensionless pure numerical values according to a preset proportion.

5. The method according to claim 1, wherein obtaining the pre-trained fitting model by fitting the objective data and the subjective evaluation comprises:
    generating, with a modeling analysis method, the pre-trained fitting model for predicting a relationship between an independent variable and a dependent variable, wherein the independent variable is the objective data of the subject recorded in real-time, and the dependent variable is the predicted subjective evaluation.

6. The method according to claim 1, further comprising: adjusting a relationship between signal instructions and an external hardware device control during the intelligent human-machine cooperation system test based on the real-time human-machine cooperation score,
    wherein the relationship between the signal instructions and the external hardware device control comprises a signal recognition threshold and a signal output gain.

7. The method according to claim 1, wherein:
    the intelligent human-machine cooperation system test is a human-machine interaction between the subject and the intelligent human-machine cooperation system;
    the intelligent human-machine cooperation system is built based on a task framework in a prototype library, a standard library, and a paradigm library;
    the task framework comprises a processor and a controller;
    the processor is configured to acquire preset types of brain signals of the subject, and extract evoked signals based on the brain signals and a Brain-Computer Interface (BCI) paradigm library and generate a control instruction based on the evoked signals; and
    the controller is configured to control an external hardware device to execute the control instruction.

8. A device for evaluating an intelligent human-machine cooperation system, comprising: a processor and a storage with computer instructions stored therein, wherein the processor is configured to execute the computer instructions stored in the storage to implement the method according to claim 1.

9. A non-transitory computer-readable storage medium with a computer program stored thereon, wherein the computer program is configured to be executed by a processor to implement the method according to claim 1.

10. A method for evaluating an intelligent human-machine cooperation system, comprising:
- recording objective data of a subject during executing, by the subject, an intelligent human-machine cooperation system test;
- inputting the objective data into a pre-trained fitting model for prediction to obtain a predicted subjective evaluation, wherein the pre-trained fitting model is obtained by fitting the objective data and a subjective evaluation, and the subjective evaluation is obtained based on a first subjective evaluation result of the subject after executing the intelligent human-machine cooperation system test for a pre-training;
- obtaining a real-time human-machine cooperation score based on the predicted subjective evaluation; and
- adjusting a relationship between signal instructions and an external hardware device control during the intelligent human-machine cooperation system test based on the real-time human-machine cooperation score,
- wherein the relationship between the signal instructions and the external hardware device control comprises a signal recognition threshold and a signal output gain.

* * * * *